(12) United States Patent
Baynham (10) Patent No.: US 9,743,959 B2
(45) Date of Patent: Aug. 29, 2017

(54) LOW PROFILE SPINAL FIXATION SYSTEM

(71) Applicant: Atlas Spine, Inc., Jupiter, FL (US)

(72) Inventor: Matthew G. Baynham, Jupiter, FL (US)

(73) Assignee: Atlas Spine, Inc., Jupiter, FL (US)

( * ) Notice: Subject to any disclaimer, the term of this patent is extended or adjusted under 35 U.S.C. 154(b) by 81 days.

(21) Appl. No.: 14/210,197

(22) Filed: Mar. 13, 2014

(65) Prior Publication Data

US 2015/0257793 A1 Sep. 17, 2015
US 2016/0302833 A9 Oct. 20, 2016

Related U.S. Application Data

(60) Provisional application No. 61/784,398, filed on Mar. 14, 2013.

(51) Int. Cl.
A61B 17/70 (2006.01)

(52) U.S. Cl.
CPC ........ *A61B 17/7041* (2013.01); *A61B 17/704* (2013.01)

(58) Field of Classification Search
CPC ....................................... A61B 17/70–17/7046
See application file for complete search history.

(56) References Cited

U.S. PATENT DOCUMENTS

| | | | |
|---|---|---|---|
| 5,129,899 A | 7/1992 | Small et al. | |
| 5,304,179 A | 4/1994 | Wagner | |
| 5,344,422 A * | 9/1994 | Frigg | 606/278 |
| 5,474,551 A * | 12/1995 | Finn et al. | 606/264 |
| 5,591,166 A | 1/1997 | Bernhardt et al. | |
| 5,628,740 A | 5/1997 | Mullane | |
| 5,741,255 A * | 4/1998 | Krag et al. | 606/264 |
| 5,928,233 A * | 7/1999 | Apfelbaum et al. | 606/261 |
| 5,984,924 A * | 11/1999 | Asher et al. | 606/264 |
| 6,050,997 A | 4/2000 | Mullane | |
| 6,123,706 A | 9/2000 | Lange | |
| 6,193,719 B1 | 2/2001 | Gournay et al. | |
| 6,267,765 B1 | 7/2001 | Taylor et al. | |
| 6,280,443 B1 * | 8/2001 | Gu et al. | 606/264 |
| 6,379,357 B1 * | 4/2002 | Bernstein et al. | 606/246 |
| 6,432,109 B1 | 8/2002 | Letendart et al. | |

(Continued)

*Primary Examiner* — Jan Christopher Merene
*Assistant Examiner* — Steven Cotroneo
(74) *Attorney, Agent, or Firm* — McHale & Slavin, P.A.

(57) ABSTRACT

A spinal fixation system that includes at least two pedicle screws and a connector plate attached to each pedicle screw with a locking nut at a first end. A rod connector member attached to a second end of each connector plate with a rod connecting member locking lock. A spinal rod connected to at least two of the rod connector members. The pedicle screw including a cup shaped member that conforms to a lower mating surface on the connector plate and the locking nut having a mating surface with the upper surface of the connector plates to provide a polyaxial connection between the pedicle screw and the connector plate. The rod connector, connecting plate, and, rod connector locking nuts having mating surfaces that allow polyaxial motion between the rod connector member and the connector plate. The spinal fixation system provides a low profile system that is more easily implanted and adjustable so as to reduce the stress to the spinal column and trauma to the surgical incision.

14 Claims, 8 Drawing Sheets

(56) References Cited

U.S. PATENT DOCUMENTS

| | | |
|---|---|---|
| 6,475,218 B2 | 11/2002 | Gournay et al. |
| 6,520,990 B1 * | 2/2003 | Ray .............................. 623/17.11 |
| 6,623,485 B2 | 9/2003 | Doubler et al. |
| 6,676,661 B1 * | 1/2004 | Martin Benlloch et al. . 606/264 |
| 6,709,434 B1 * | 3/2004 | Gournay et al. ............. 606/266 |
| 6,755,830 B2 * | 6/2004 | Minfelde et al. ............. 606/278 |
| 6,783,527 B2 | 8/2004 | Drewry et al. |
| 6,786,907 B2 | 9/2004 | Lange |
| 6,875,215 B2 | 4/2005 | Taras et al. |
| 6,945,972 B2 * | 9/2005 | Frigg et al. ................... 606/256 |
| 6,997,927 B2 | 2/2006 | Jackson |
| 7,018,379 B2 | 3/2006 | Drewry et al. |
| 7,179,261 B2 | 2/2007 | Sicvol et al. |
| 7,204,838 B2 | 4/2007 | Jackson |
| 7,255,700 B2 | 8/2007 | Kaiser et al. |
| 7,316,532 B2 | 1/2008 | Matthys-Mark |
| 7,578,833 B2 | 8/2009 | Bray |
| 7,585,312 B2 * | 9/2009 | Rawlins et al. .............. 606/246 |
| 7,594,924 B2 * | 9/2009 | Albert et al. ................. 606/267 |
| 7,708,762 B2 | 5/2010 | McCarthy et al. |
| 7,766,911 B1 * | 8/2010 | Navarro et al. ................ 606/71 |
| 7,850,719 B2 * | 12/2010 | Gournay et al. ............. 606/278 |
| 2002/0049446 A1 * | 4/2002 | Harkey et al. ................. 606/70 |
| 2007/0270859 A1 | 11/2007 | Companioni et al. |
| 2008/0275456 A1 * | 11/2008 | Vonwiller .......... A61B 17/7032 606/246 |
| 2008/0306551 A1 | 12/2008 | Sanders et al. |
| 2010/0268279 A1 * | 10/2010 | Gabelberger et al. ........ 606/278 |
| 2011/0004251 A1 * | 1/2011 | Sweeney et al. ............. 606/264 |
| 2012/0029566 A1 * | 2/2012 | Rezach ......................... 606/264 |
| 2012/0150232 A1 * | 6/2012 | Van Nortwick et al. ..... 606/264 |

\* cited by examiner

LOW PROFILE SPINAL FIXATION SYSTEM

PRIORITY CLAIM

In accordance with 37 C.F.R. 1.76, a claim of priority is included in an Application Data Sheet filed concurrently herewith. Accordingly, the present invention claims priority to U.S. Provisional Patent Application No. 61/784,398, entitled "Low Profile Spinal Fixation System", filed Mar. 14, 2013. The contents of which the above referenced application is incorporated herein by reference in its entirety.

FIELD OF THE INVENTION

The present invention relates to a spinal fixation system for the immobilization of spinal bone bodies. The spinal fixation system allows the implantation of the pedicle screws at the preferred anatomical locations and orientation while providing connections between the rod and screws with a minimal amount of force required to the spine or components of the system during assembly. The spinal fixation system provides easier access and installation as well as a low profile to reduce tissue inflammation and surgical trauma.

BACKGROUND OF THE INVENTION

The spine is a complex structure of vertebral bones and connective tissues. The vertebral bodies, discs and ligaments are configured in operative engagement to perform flexibility for motion, support for body forces and protection for the spinal cord. The structure and functionality of this complex arrangement can be compromised if one or more components are diseased or injured. Often it is possible to treat these problems with conservative non surgical methods such as physical therapy, medication and or exercise. In other instances, such as degenerative instability, deformity, trauma, tumors, etc., necessitate surgical intervention to treat unstable vertebral joints and treat pain caused by root compression.

There are a variety of surgical procedures that result in fixation of portions of the spine to one another. In most instances fixation of the spine involves the use of bone screws. These screws are implanted through surgical openings in adjacent portions of the spine and threaded into the spine members. The bone screws are then mechanically connected through additional components such as rods and plates.

A number of internal spinal fixation systems have been used in spinal surgery to achieve a rigid fixation. A common technique is the use of posterior implants using pedicle screws coupled to longitudinal rods. Typically posterior implants include a one or more pairs of rods that are positioned along the longitudinal axis of the spine. These rods are attached to the spinal column by bone screws that are threaded into the pedicles of the individual vertebral bodies. The procedure for posterior fixation includes the steps of insertion of the screws into the pedicles in a particular angle and depth, temporarily coupling the rods to the screws, correction of the spinal curve, and the securing of the connection rods to the screws for rigid fixation. The alignment of the pedicle screws is predicated upon the angle and depth of screw insertion which is dependent by the patient's anatomical and pathological conditions that may vary at different spinal levels as well as between patients. A lack of proper alignment will cause considerable difficulty during this procedure. Attempts to compensate for this lack of alignment can result in the creation of undesirable forces being applied to the spinal column via the pedicle screws and will extend the time needed to perform the operation, thereby increasing the possibility of complication associated with surgery. While the surgeon can form a bend in the rod or plate to ensure that the screws are firmly secured to the plate or the rod, such a modification may create stresses that may result in the vertebrae to fracture or the screws to loosen over a period of time. Therefore is highly desirable that the bone fixation system minimizes the possibility of creating unnecessary excessive loads on the spinal column.

DESCRIPTION OF THE PRIOR ART

One example of a spinal fixation assembly can be seen in U.S. Pat. No. 5,219,899, to Small et al, that discloses a surgical spinal fixation system including a bone bolt having first end portions that are adapted to be surgically implanted into a patient's spine at first and second spaced apart positions and a central portion of the bone bolt defining a load transfer surface, the bone bolt having a second upper threaded sections for threadably receiving a nut at a shaped, countersunk interface. As an alternate embodiment, a bone screw provides an upper enlarged head with a lower coarsely threaded shank. A plate having upper and lower surfaces and outer opposed edges is provided with an elongated slot for accommodating a selected bone bolt or bone screw. The plate edges carry fine adjustments extending between the upper and lower surfaces of the plate and a load transfer washer interfaces the plate and the selected bone bolt or bone screw for distributing load (and reducing stress) from the bone bolt (or screw) to the plate.

U.S. Pat. No. 5,304,179, to Wagner, discloses a spinal fixation system for installing spinal instrumentation posterior to a patient's spine to fuse selected vertebrae. The spinal fixation system includes a plurality of connectors and associated bushings. The connectors comprise a first portion canted at an angle of 7.5 degrees relative to a second portion. The connectors secure to the spinal instrumentation to the pedicle screws. Each bushing contains an angled borehole. The combination of the angles produced by the connectors and the boreholes of each the bushings allow the installation of the pedicle screws at various angles relative to the patients' spine.

U.S. Pat. No. 5,591,166, to Bernhardt et al, discloses an orthopedic bone bolt and bone plate construct comprising a bone plate and a series of fasteners. The bone plate member has at least one open positions, with the open positions allowing placement of a series of fasteners there through at spaced apart positions along the length of the open portions. The series of fasteners are attachable to the plate member at the open positions, with at least one of the fasteners including a multi-angle fastener having a pair of fastener sections configured to be angled relative to one another. The multi-angle fastener comprising; and upper section having a central longitudinal axis and an outer surface; a lower section having a central longitudinal axis and an outer surface with a threaded portion configured to be surgically implantable into a patient's bone tissue and a joint for connecting the upper and lower sections together. The joint including corresponding mating surfaces configured to articulate with each other sufficiently to allow the upper and lower sections to angle relative to one another.

U.S. Pat. No. 5,628,740, to Mullane, discloses a toggle bolt bone screw for use in surgical implants having particular usefulness in the stabilization of the human spine by fixation of vertebra. The apparatus employs a self-tapping anchoring screw having a ball joint socket for receipt of a rotatable threaded bolt. The ball joint allows angular placement of the bolt which is secured into position by an attachment nut coupling directly to the anchoring screw. An upper surface of the attaching nut is rounded allowing engagement of component devices. A rod clamp is disclosed for use in combination with the device providing attachment to support rods and serving to bias the bolt into a permanent fixed position upon attachment. An alternative embodiment is disclosed of the rod clamp providing a single support rod attachment system.

U.S. Pat. No. 5,984,924, to Asher et al, a bone alignment assembly having bone anchor subassemblies for securing to both bones and bone position retainer, wherein the bone position retainer includes a longitudinal member for maintaining a desired alignment of the bones when the bone anchor assemblies are secured to the bone position retainer. Each of the bone anchor subassemblies includes a shaft and one or more pairs of components (e.g. washers) wherein the components of each pair have mating spherical concave and convex surfaces that can mate together in a plurality of angular positions. When the shaft extends through each of the pairs of mating components, and also through a passageway of the bone position retainer that is sandwiched between the two pairs of mating components, the shaft can be secured at any one of a plurality if orientations relative to the bone position retainer.

U.S. Pat. No. 6,050,997, to Mullane, is directed to a spinal fixation system comprised if a collection of anchoring assemblies attached via a variety of connectors, to spine stabilization rods. The anchoring assemblies include a linking member attached in a ball and socket fashion to a bone engaging member that is adapted to engage a spinal bone of a patient. The linking member joins one of the included connectors to an associated bone engaging member. The connectors are selectively attached to on of the stabilizing rods. The anchoring assemblies each include a support collar and a retention collet that cooperate to allow adjustment of the bone-engaging member and corresponding connector during surgery. When surgery is complete, a securing nut and locking bolt cooperate with the support collar and retention collet to maintain the relative position of the entire fixation system, preventing unwanted movement between the system components. In one embodiment, the connectors are multi-piece units that may be added or removed with disturbing adjacent connectors.

U.S. Pat. No. 6,123,706, to Lange, is directed to a support system for stabilizing the spine. The system includes a spinal rod, at least two connectors slidable along the rod, at least two pedicle screws for fixation to a healthy pedicle bone on either side of the vertebrae to be repaired, and a one piece clamping member connecting the pedicle screws to the rod and supporting the connector for limited pivoting movement with respect to the screws and accurate positioning if the rod with respect to the pedicle screws.

U.S. Pat. No. 6,267,765, to Taylor discloses an osteosynthesis device that includes at least two bone anchoring elements in the vertebral bone structures, a longitudinal linking member between the bone anchoring elements, and connector links between the bone anchoring elements and said linking members. Each bone anchoring element includes a bond fixing part, a head to be gripped by a screwing device, a threaded shaft extending the grip head and a clamping elements to be screwed on said shaft to lock together the connector link, the longitudinal linking member and the corresponding bone anchoring element; the threaded shaft is provided at its end with a hinge ball joint in a housing if the grip head, enabling a multidirectional adjustment of the shaft and a positioning of the connector link.

U.S. Pat. No. 6,280,443, to Gu et al, discloses a spinal fixation system for use in the immobilization of a sequence of spinal bones, comprising a plurality of pedicle screws, a pair of rods, and connectors. The pedicle screw has a spherical head having a round portion at an upper portion of the spherical head, a threaded shaft for insertion through the pedicles, and a threaded stem on the top of the spherical head. The connector has a rod passage for receiving the rod there through, a set member bore formed in an upper portion of the connector, and a support portion having an opening formed for adapting the stem of the pedicle screw and a recessed hemispherical wall. A spherical joint at the pedicle screw and the connector allows the multidirectional adjustment capability of the connector so that the screws can be implanted in any angulation with no need of having the screws well aligned. The spherical head of the pedicle screw and the hemispherical wall have slightly different diameters which improve the locking power and provide a rigid fixation. A rigid coupling is achieved between the rod and the connector by making the cross-section of the rod passage as an imperfect circular shape which allows the three point contact between the rod and the rod passage. The assembly is locked in place by tightening a fixing cap and a set member from the posterior aspect of the spine.

U.S. Pat. No. 6,432,109, to Letendart et al, discloses an ostheosynthesis connection device designed to connect a screw for implanting in the spine to a vertebral support rod. The screw is constituted by a bottom first threaded portion, a head having flats and a curved base, and a top second threaded portion in line with the first. A nut having a curved base is suitable for co-operating with the second threaded portion. For connection with the screw, a connection piece has a hole of inside diameter that is greater than the outside diameter of the second threaded portion of the screw, and around said hole it has curved top and bottom bearing faces such that the connection piece is locked in position relative to the screw once the nut has been tightened by the curved base of the nut bearing against the top bearing face thereof and by the bottom bearing face being clamped against the curved base of the head of the screw.

U.S. Pat. No. 6,623,485, to Doubler et al, is directed to a spinal fixation system that includes a collection of anchoring assemblies attached, via a variety of connectors, to spine stabilizing rods. The anchoring assembly includes a linking member attached in a ball and socket fashion to a bone engaging member that is adapted to engage a spinal bone of a patient. The linking member joins one of the included connectors to an associated bone engaging member. The connectors are selectively attached to one of the stabilizing rods. The anchoring assemblies each include a support collar and a split retention ring that cooperate to allow adjustment of the bone engaging member and corresponding connector during surgery. When surgery is complete, a securing nut an locking bolt cooperate with the support collar and the split retention ring to maintain the relative position of the entire fixation system, thereby preventing unwanted movement between the system components.

In addition, U.S. Pat. No. 6,709,434, to Gournay et al, discloses a spinal osteosynthesis device comprising a bone anchorage element a vertebral rod, a connector for interconnecting the rod and the anchorage so that the anchorage element is capable of being angularly oriented in a polyaxial manner relative to the rod. A fixation element is provided for fixing the position of the connector in translation and in rotation relative to the rod. A clamp element is provided for clamping the bone anchorage element to the connector is a predetermined angular position independent of the fixation element.

U.S. Pat. No. 7,578,833, to Bray, discloses an assembly, comprising a bone fastener, an adjusting member and a securing fastener for fastening an appliance to a bone body so that a plurality of the bone fastener assemblies and the appliance constitute an apparatus that retain a plurality of bone bodies. Each fastener has an attaching portion for attaching the bone fastener to a bone body, a supporting portion for supporting the adjusting member for universal movement relative to the supporting portion, and a securing portion for securing the bone fastener to the fastener. The fastener has a first end that passes through an aperture in the appliance and an opening in the adjusting member and is secured to the securing portion of the bone fastener. A second end of the fastener has a bearing surface that adjustably bears against the appliance in opposition to an engaging surface of the adjusting member that engages the appliance. Bray shows a pedicle screw with a concave surface 41 on the screw head with a convex locking member 44.

U.S. Pat. No. 7,708,762, to McCarthy et al., discloses a system for stabilization of the spinal column, including an elongate support member extending along an axis and a plurality of anchor members configured for anchoring to respective vertebrae. A first of the anchor members is engaged to the support member in a manner that substantially prevents axial movement of the support member relative to the first anchor member, and a second of the anchor members is engaged to the support member in a manner that allows substantially unconstrained axial movement of the support member relative to the second anchor member. In a further embodiment, a third of the anchor members are engaged to the support member in a manner that also allows substantially unconstrained axial movement of the support member relative to the third anchor member, with the second and third anchor members positioned on opposite sides of the first anchor member.

U.S. Published Application No. US 2008/030655, to Sanders et al., discloses a surgical fastening (160), kit of parts including the fastening and method for stabilizing a vertebra using the fastening is described. The fastening is used to attach a rod (166) to a spinal body part. The fastening comprises a split ring (160) of a material which defines a channel for receiving the rod. A formation can receive a fixing (168) to secure the fastening to the spinal body part. A closure mechanism is operable to close the ring. The material is sufficiently flexible to allow the fastening to be closed about the rod at least once, without weakening.

U.S. Published Patent Application 2007/0270859, to Companioni, discloses break off screws configured so that when one head or screw portion is broken off, a complete screw with head remains.

Nevertheless, using these devices does not provide a spinal fixation system that can be easily and accurately implanted without placing undo stress forces on the spinal column and maintain a low profile thereby reducing tissue inflammation and surgical trauma.

SUMMARY OF THE INVENTION

Therefore, it is the primary object of the present invention to provide a low profile spinal fixation system that is more easily implanted and adjusted so as to reduce the stress to the spinal column and trauma to the surgical incision.

Accordingly, it is an objective of the instant invention to provide a spinal fixation system that is easily inserted into the wound as the assembly is positioned down detachable guide wired and directly onto the screws.

It is a further objective of the instant invention to provide a low profile fixation system that reduces the amount of tissue inflammation and surgical trauma.

It is still another objective of the instant invention to provide a spinal fixation system that does not require rod bending to conform to anatomic anomalies of the spine and provides a high degree of conformity to the anatomy of the posterior spine.

It is yet another objective of the instant invention to provide tension rings inside the rod bores to frictionally hold the rod thereby increasing handling ability and easing construct assembly.

It is a still further objective of the invention to provide a fixation system with modularity thereby allowing increased visibility in situ by removing the head while placing the screw.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

Figure 1:
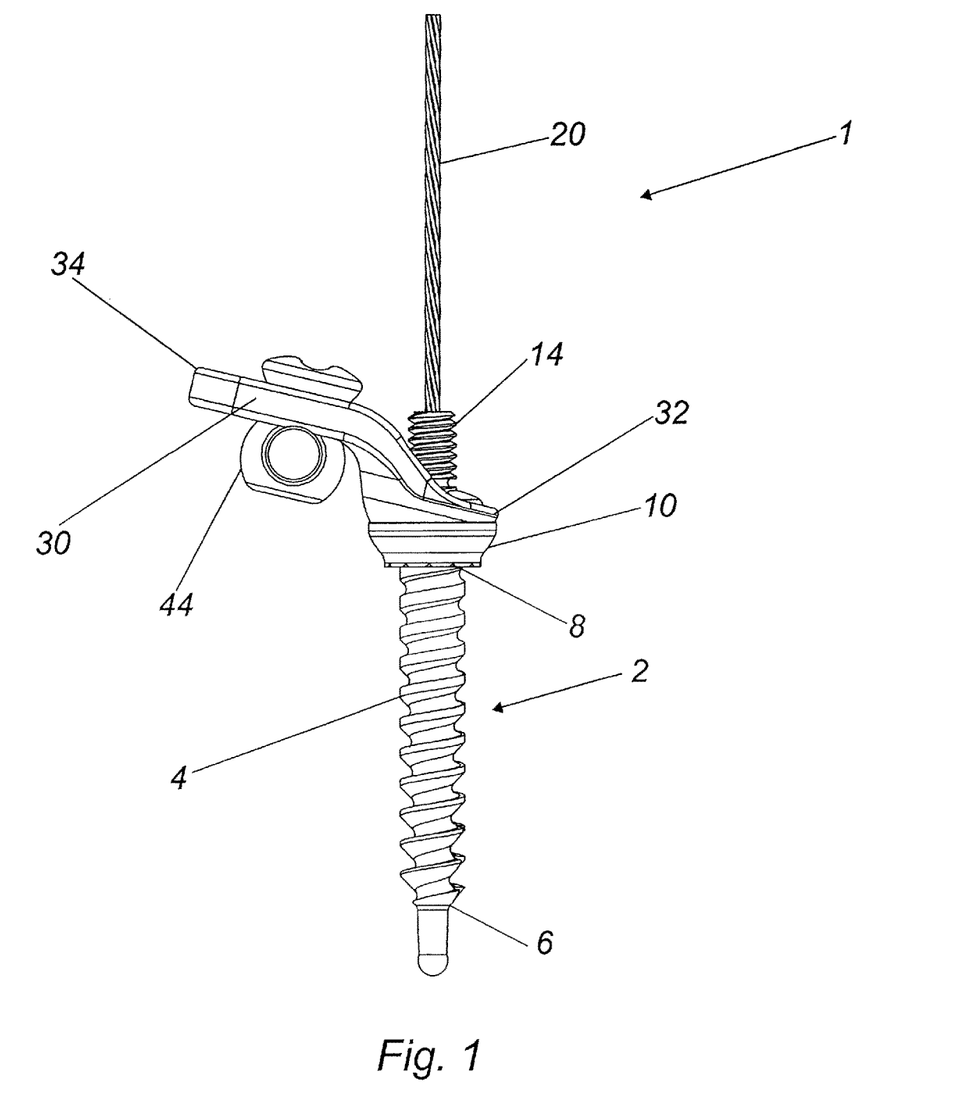
FIG. 1 is a side view of the spinal fixation system

FIG. 1 is a side view of the spinal fixation system. The spinal fixation system 1 includes a pedicle screw 2. The pedicle screw 2 includes a first set of threads 4 that are sized and configured to be screwed into individual pedicles located on the vertebral bodies. The threads 4 have a distal end 6 and a proximal end 8. A cup shaped receiver 10 is formed integral with pedicle screw 2 adjacent the proximal end 8. The cup shaped receiver 10 includes a concave mating surface 12 as can be seen in the cross sectional view shown in FIG. 2. Also formed on pedicle screw 2 is a second set of threads 14. The second set of threads 14 extends from a position spaced from the cup shaped receiver 10 and extends to the uppermost portion of the pedicle screw 2 located at the end opposite the distal end of the screw 2. A locking nut 16 includes a threaded central aperture 18. The second set of threads 14 is sized and configured to operatively engage the threads 18 formed on central aperture of locking nut 16. The screw 2 is threaded into a vertebral body with a wire 20 secured to the proximal end of the screw 2. Alternatively, a cannulated screw can be guided into position with the assistance of a K-wire, not shown.

Figure 2:
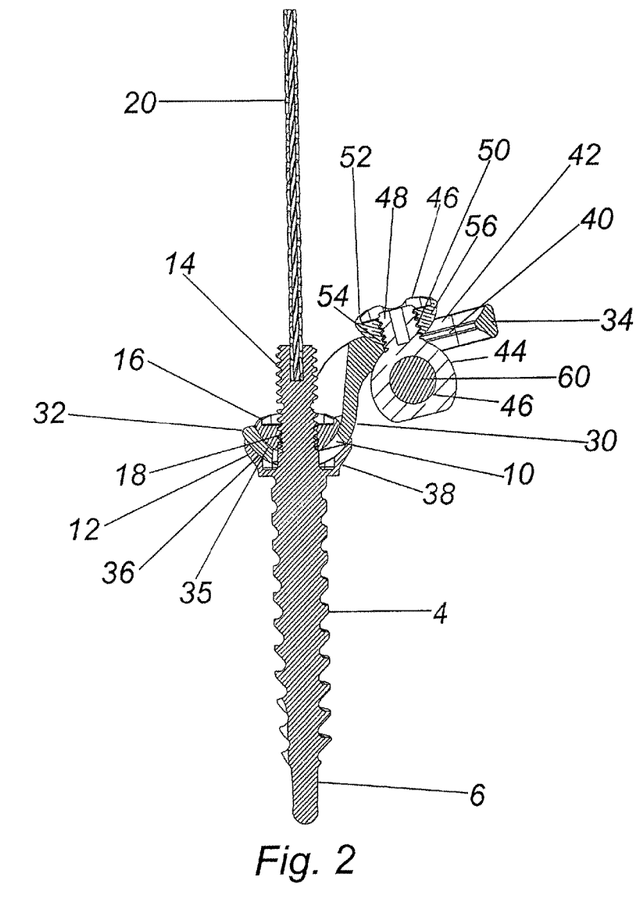
FIG. 2 is a cross sectional side view of the spinal fixation system.

A connector plate 30 has a first end 32 and a second end 34. The first end 32 includes an upper concave surface 35 and a lower convex surface 36. Once the locking nut 16 is threaded into contact with the connector plate 30 the upper concave surface 35 forms a mating surface with a convex surface 38 formed on a lower portion of locking nut 16. In a like fashion the lower convex surface 36 on the first end 32 of the connector plate 30 forms a mating surface with the concave mating surface 12 formed on the cup shaped receiver 10. The operative engagement between the cup shaped receiver 10, the upper mating surface 35, lower mating surface 36 of the connector plate 30 and the convex surface mating surface 38 on the lower surface of the locking nut 16 provides a polyaxial connection between the pedicle screw 2 and the connector plate 30. The connector plate 30 has a length, a width and a thickness. Along its length the connector plate 30 includes a curved surface wherein the first end 32 is in a lower horizontal plane relative to a horizontal plane of the second end 34.

At the second end 34 of the connector plate 30 is a slot 40. The slot 40 is oblong in shaped and includes a concave inner edge surface 42 around its perimeter. The spinal fixation system 1 includes a spinal rod 60 that is connected to the connector plate 30 with a rod connector member 44 and a rod connector locking nut 46. The rod connector member 44 includes an aperture 46 that has a diameter just slightly larger than the diameter of the spinal rod 60 thereby allowing relative rotary motion between the rod 60 and rod connector member 44 under the application of force. Tension ring 47 mounted within the aperture 46 provides a friction fit between the rod connector member 44 and the rod 60 to increase the handling ability of the spinal assembly 1 and improve the ease of construct. The upper portion of rod connector member 44 includes a post 48. Post 48 has a set of threads 50 formed on the outer cylindrical surface of the post 48. A rod connector member locking nut 52 has a threaded central aperture. The threads 54 are sized and configured to operatively engage threads 50 formed on the post 48. Rod connector member locking nut 52 has a lower convex surface 56 that is sized and configured to mate with the concave inner edge surface 42 around the perimeter of slot 40. The operative engagement between the inner edge surface 42 and the lower convex surface 56 of the rod connector member locking nut 52 provides a polyaxial connection between the spinal rod 60 and the connector plate 30.

The spinal assembly 1 includes two or more pedicle screws 4 and associated connector plates 30, locking nuts 16 and 52 and rod connector members 44 are interconnected by a spinal rod 60. Typically posterior implants include a one or more pairs of rods that are positioned along the longitudinal axis of the spine. These rods are attached to the spinal column by bone screws that are threaded into the pedicles of the individual vertebral bodies.

Figure 3:
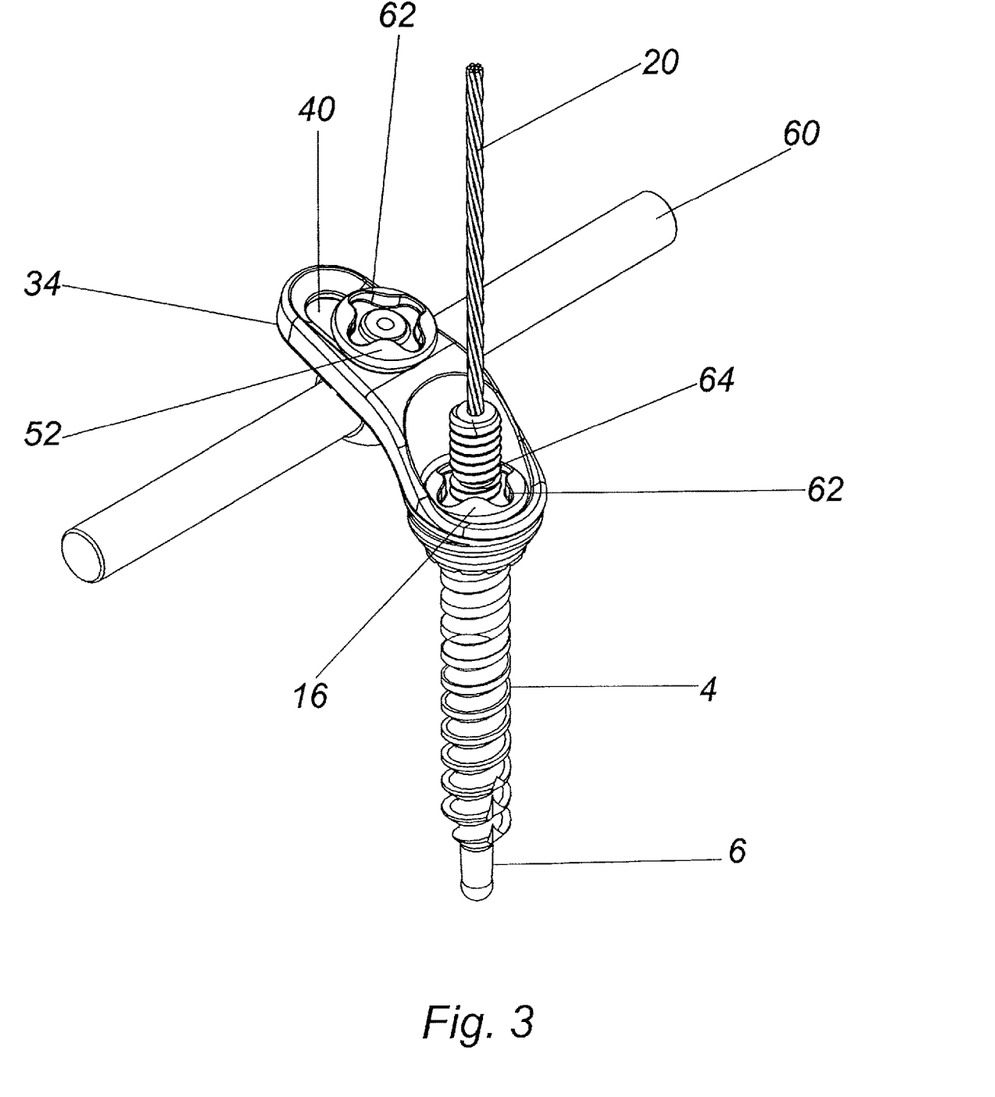
FIG. 3 is a top perspective view of the spinal fixation system

As shown in FIG. 3, locking nut 16 and rod connector member locking nut 52 each include a recess 62 formed in their upper surfaces that are dimensioned to operatively engage a distal end of a tool that will impart rotation thereto and cause the locking nut and rod locking nut to be threaded into position. The pedicle screw 4 can either have a wire 20 attachment that is sheared off after it is used or the screw can be cannulated and inserted by K-wire. The upper portion of the pedicle screw 4 includes a weaken area 64 located in the area of the second set of threads 14 that permits the upper end to be broken off after it is no longer needed so as to provide a low profile for the pedicle screw 4.

The screws are either positioned by K-wire through a cannulated pedicle screw or include a wire 20 attached to the proximate end of the screw 4. The connector plate 30, rod 60, rod connector member 44 and rod connector member locking nut 52 are assembled outside of the body and are then placed into position using one or more guide wires. The assembly is easily inserted into the wound as it is dropped down detachable guide wires and right on to the pedicle screws 4. The ability to infinity position and the rod relative to the pedicle screws eliminates the need for rod bending to conform to the anatomic anomalies of the spine and provides a high degree of conformity to the anatomy of the posterior spine.

Figure 4:
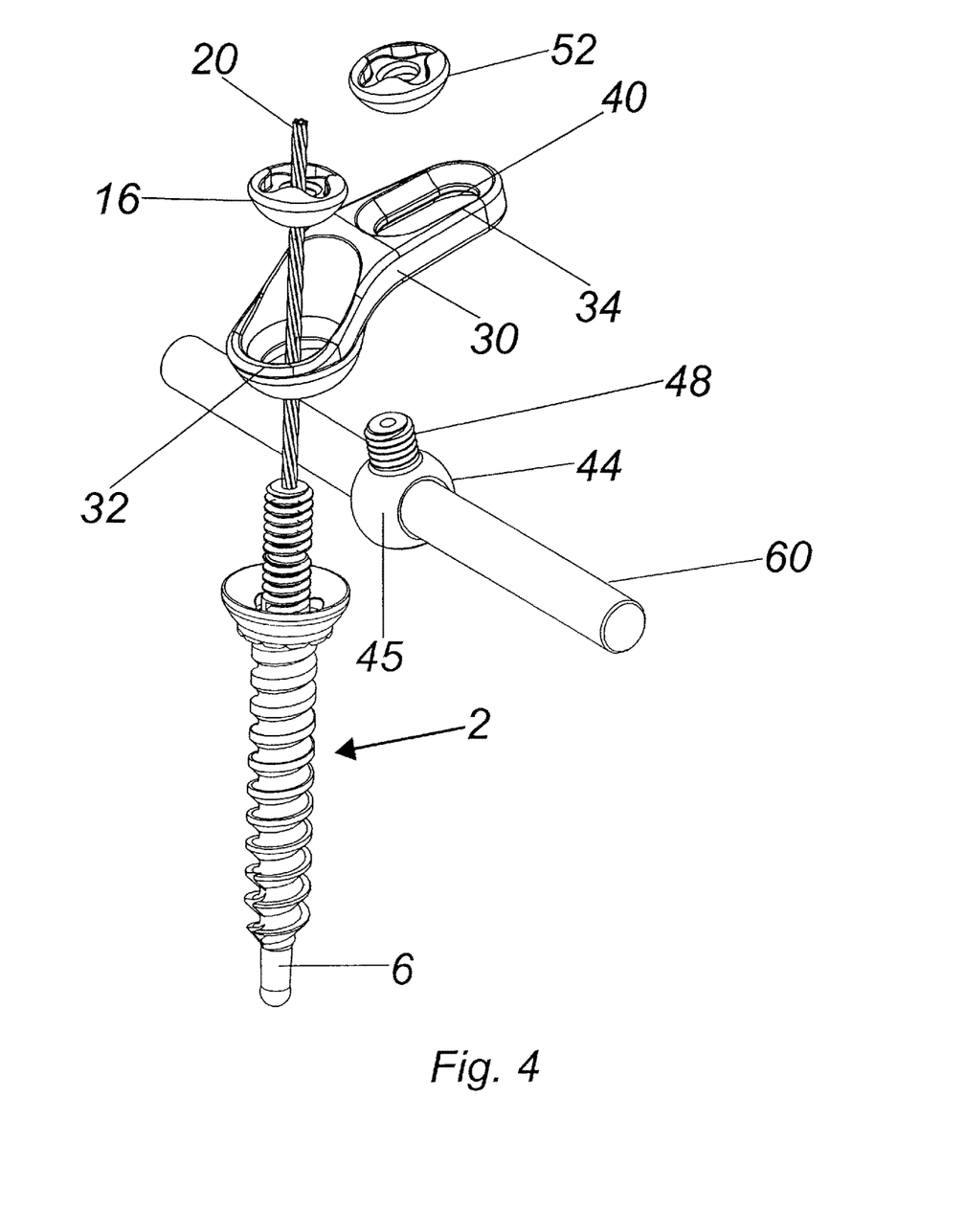
FIG. 4 is a partially exploded top perspective view of the spinal fixation system.

FIG. 4 is an exploded view of the spinal assembly with the individual components separated for the purposes of clarity.

Figure 5:
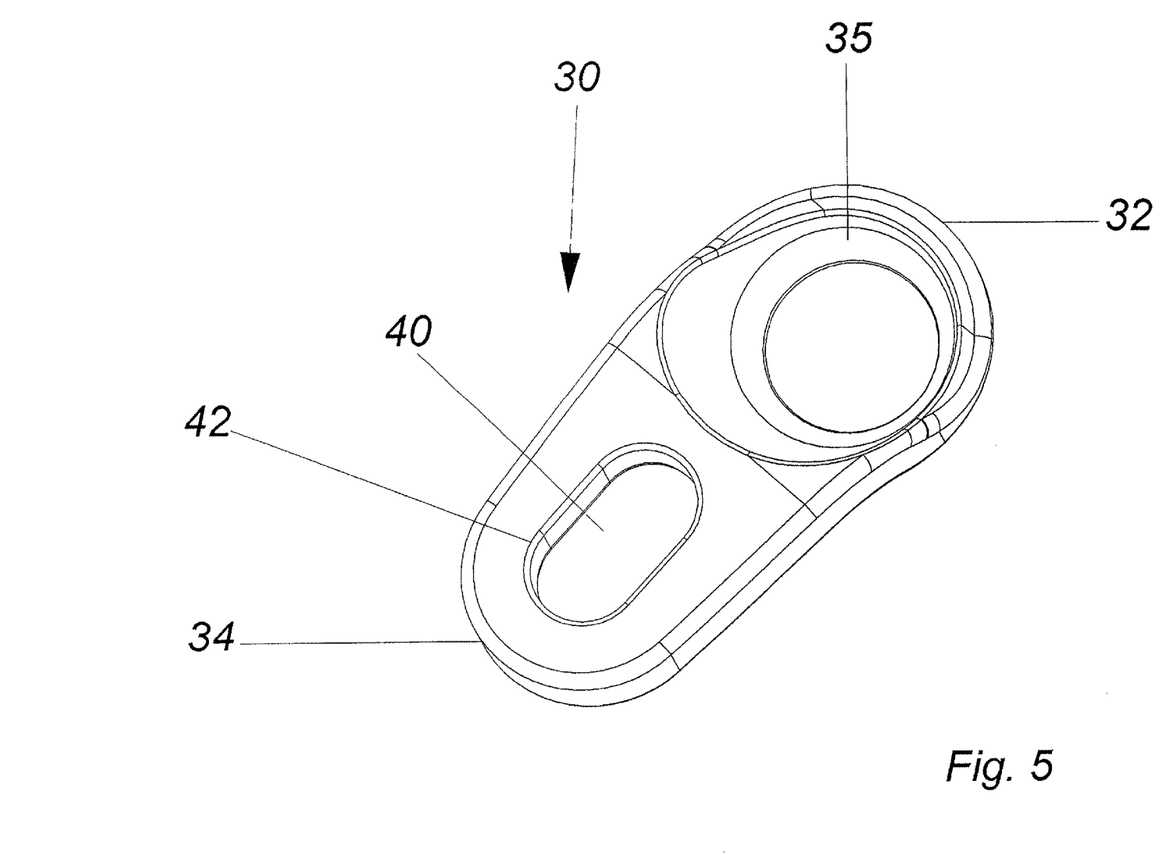
FIG. 5 is a top perspective view of a connector of the spinal fixation system.

FIG. 5 is a top perspective view of the connector plate 30 of the spinal fixation system 1. As shown, the connector plate 30 has a first end 32 and a second end 34. The first end 32 includes an upper concave surface 35. The second end 34 of the connector plate 30 includes a slot 40. The slot 40 is oblong in shaped and includes a concave inner edge surface 42 around the upper surface of the perimeter of the slot 40.

Figure 6:
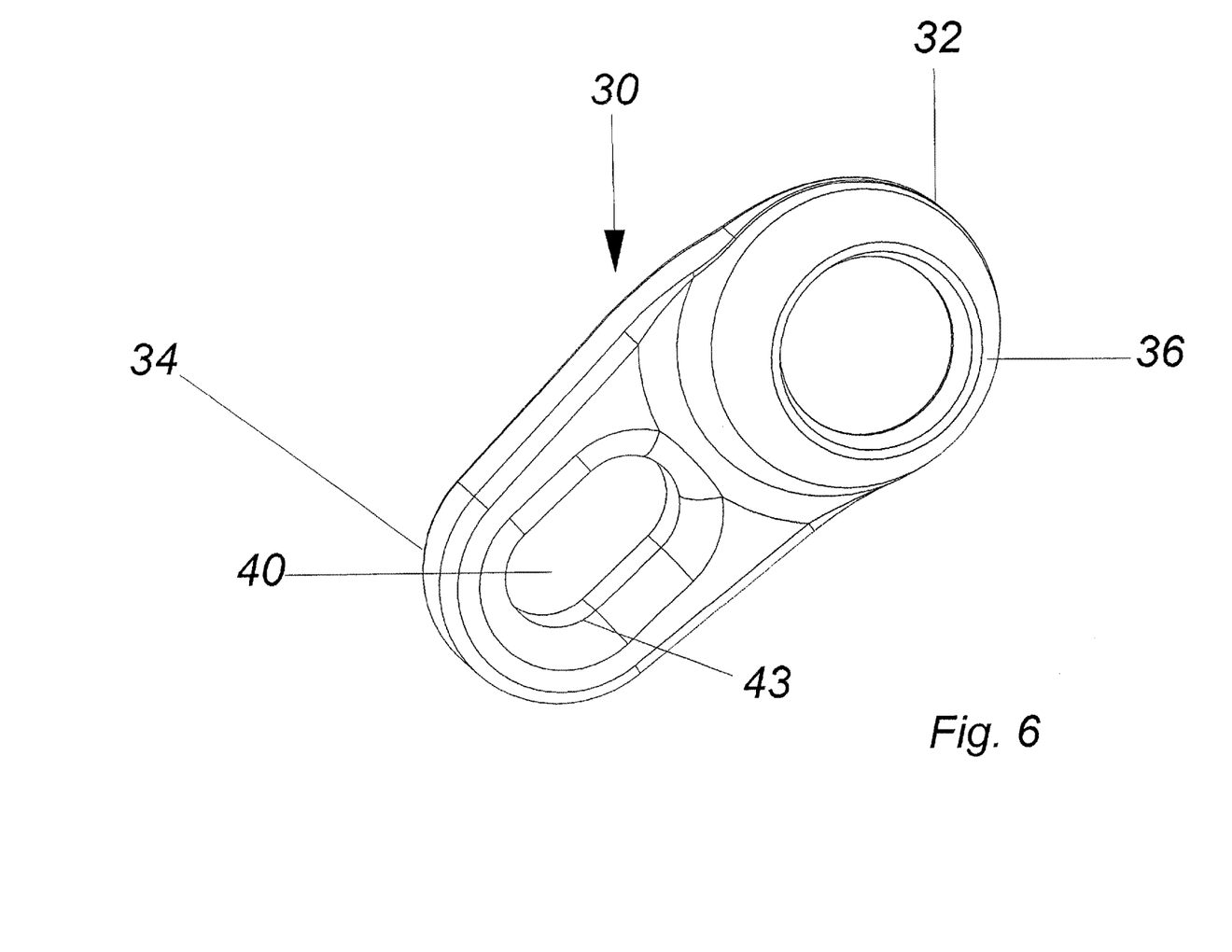
FIG. 6 is a bottom perspective view of a connector of the spinal fixation system.

FIG. 6 is a bottom perspective view of the connector plate 30 of the spinal fixation system 1. As shown the connector plate 30 includes a lower concave surface 36 at the first end 32 of connector plate 30. The slot 40 has a concave surface 43 located around the lower surface of the perimeter of slot 40. The concave surface 43 is configured to conform to the spherical surface 45 on rod connector member 44.

Figure 7:
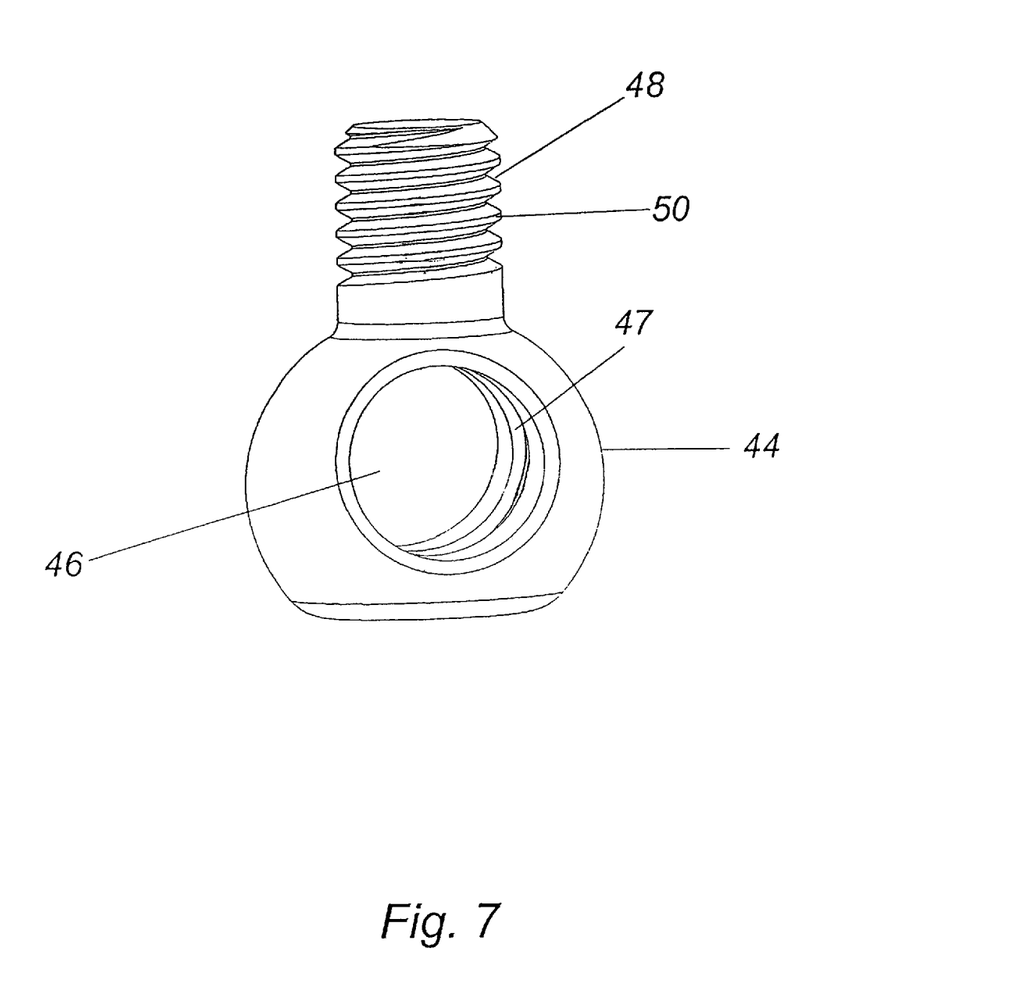
FIG. 7 is a perspective view of a rod connector.
Figure 8:
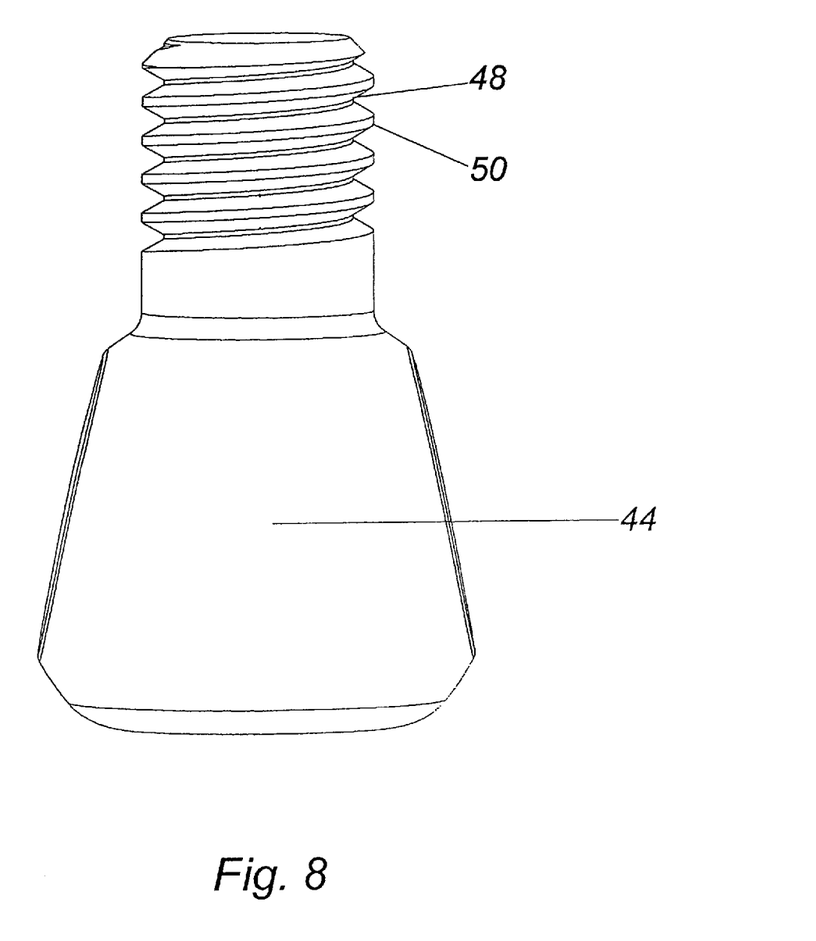
FIG. 8 is a cross sectional view of the rod connector.

FIG. 7 is a perspective side view of the rod connector member 44. As shown, the rod connector member 44 includes a post having external threads 50. The threads 54 on the rod connector member locking nut 52 are sized and configured to operatively engage threads 50 formed on the post 48. The rod connector member 44 includes an aperture 46 that has a diameter just slightly larger than the diameter of the spinal rod 60 thereby allowing relative rotary motion between the rod 60 and rod connector member 44 under the application of force. Tension ring 47 mounted within the aperture 46 provides a friction fit between the rod connector member 44 and the rod 60 to increase the handling ability of the spinal assembly 1 and improve the ease of construct. FIG. 8 is also a perspective side view of the rod connector member 44 with the longitudinal axis of aperture 46 oriented perpendicular to this view.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A spinal fixation assembly comprising:
   a first pedicle screw and a second pedicle screw, each said pedicle screw is defined by a distal end having a first set of threads constructed for fastening to a vertebral body and a proximal end having a second set of threads with a frangible area, a guide wire extending from said proximal end;
   a first connector plate attached to said first pedicle screw and a second connector plate connected to said second pedicle screw;
   a first rod connector member attached to said first connector plate and a second rod connector attached to said second connector plate;
   a spinal rod attached to both said first rod connector member and said second rod connector member;
   said first and said second pedicle screws each including a cup shaped receiver;
   each cup shaped receiver including a concave mating surface;
   said first connector plate having a first end and a second end;
   said second connector plate having a first end and a second end;
   said first end on each of said first and second connector plates including an upper concave surface and a lower convex surface;
   the second end on each of the first and second connector plates including an upper concave surface and a lower concave surface,
   the lower convex surface on said first end of said first and second connector plates is in operative engagement with the concave mating surface on each of the cup shaped receivers on the first and second pedicle screws;
   and the lower concave surface on the second end of said first and second connector plates is in operative engagement with a spherical surface on each of said first and second rod connector members,
   whereby said concave and convex mating surfaces that form connections between the first pedicle screw and first connector plate, the second pedicle screw and the second connector plate, the first rod connector member and the first connector plate and the second rod connector member and the second connector plate provide polyaxial movement of said pedicle screws and said rod connector members, said guide wire allows ease of placement of said plates and is detached along said frangible area after said locking nuts are secured.

2. The spinal fixation assembly of claim 1 further comprising:
   a third pedicle screw, a third connector plate attached to said third pedicle screw, a third rod connector member attached to said third connector plate, wherein said third rod connector member is to attached to said spinal rod.

3. The spinal fixation assembly of claim 2 further comprising four or more pedicle screws, four or more connector plates, and four or more rod connector members, said spinal rod being attached to each of said four or more rod connector members.

4. The spinal fixation assembly of claim 3 further wherein each of said pedicle screws includes a first set of threads that are sized and configured to be threaded into a vertebral body and a second set of threads that are designed and configured to cooperate with threads on a locking nut, said second set of threads including a frangible area.

5. The spinal fixation system of claim 4 wherein each of said locking nuts includes a lower convex surface that is configured to mate with said upper concave surface on the first end of the connector plate, said locking nut further including an upper surface that is dimensioned to operatively engage a distal end of a tool that will impart rotation thereto and cause the locking nut to be threaded into position.

6. The spinal fixation system of claim 4 wherein each of said pedicle screws includes a guide wire secured to an end of each of said pedicle screws.

7. The spinal fixation system of claim 4 wherein each of said pedicle screws includes a frangible area located in the area of the second set of threads wherein the upper end of the pedicle screw can be removed after it is no longer needed so as to provide a low profile for the pedicle screw.

8. The spinal fixation assembly of claim 1 further wherein each of said rod connector members includes a post with a conical shaped base, said post having an external set of threads thereon, said post being sized and configured to pass through a slot formed in the second end of each of said connector plates, said conical shaped base constructed and arranged to mate polyaxially with said slot.

9. The spinal fixation assembly of claim 8 wherein each of said rod connector members includes a rod connector member locking nut, each of said rod connector locking member locking nuts including a lower convex surface that is configured to mate with the upper concave surface located on the second end on each of said connector plates.

10. The spinal fixation assembly of claim 9 wherein each of said rod connector members spherical surface is configured to mate with the lower concave surface on the second end of each of said connector plates.

11. The spinal fixation assembly of claim 8 wherein each of said rod connector members includes an aperture that is sized to allow said spinal rod to pass there through, each said spinal rod having a conical shaped base constructed and arranged to provide polyaxial securement to said rod connector members.

12. The spinal fixation system of claim 11 wherein said aperture of each of said rod connector members includes a groove, each of said rod connector members further includes a tension ring mounted within the said groove within said aperture, wherein a friction fit between each of the rod connector members and the spinal rod to increase the handling ability of the spinal assembly and improve the ease of construct.

13. The spinal fixation assembly of claim 8 wherein each of said posts includes a bore to secure a guide wire thereto.

14. The spinal fixation assembly of claim 1 wherein the connector plate includes a curve and the first end is positioned in a horizontal plane that is lower than a horizontal plane of the second end.

* * * * *